United States Patent
Kursar

(10) Patent No.: US 12,304,424 B2
(45) Date of Patent: May 20, 2025

(54) VEHICLE SYSTEMS FOR DYNAMIC CROWDSOURCED DELIVERY

(71) Applicant: Toyota Connected North America, Inc., Plano, TX (US)

(72) Inventor: Brian M. Kursar, Fairview, TX (US)

(73) Assignee: Toyota Connected North America, Inc., Plano, TX (US)

(*) Notice: Subject to any disclaimer, the term of this patent is extended or adjusted under 35 U.S.C. 154(b) by 1071 days.

(21) Appl. No.: 16/938,317

(22) Filed: Jul. 24, 2020

(65) Prior Publication Data
US 2021/0300297 A1 Sep. 30, 2021

Related U.S. Application Data

(60) Provisional application No. 63/001,220, filed on Mar. 27, 2020.

(51) Int. Cl.
*B60R 25/23* (2013.01)
*A61L 2/00* (2006.01)
(Continued)

(52) U.S. Cl.
CPC ............ *B60R 25/23* (2013.01); *A61L 2/0047* (2013.01); *A61L 2/10* (2013.01); *A61L 2/26* (2013.01);
(Continued)

(58) Field of Classification Search
CPC ....... B60R 25/23; B60R 9/065; B60R 16/033; B60R 25/01; B60R 25/403; B60Q 3/30;
(Continued)

(56) References Cited

U.S. PATENT DOCUMENTS

| 5,025,964 | A | 6/1991 | Phirippidis |
| 5,469,999 | A | 11/1995 | Phirippidis |

(Continued)

FOREIGN PATENT DOCUMENTS

| CN | 201290911 Y | 8/2009 |
| CN | 205574786 U | 9/2016 |

(Continued)

OTHER PUBLICATIONS

Final Office Action for U.S. Appl. No. 16/938,289 mailed on Oct. 26, 2023, 37 pages.
(Continued)

*Primary Examiner* — Navid Z. Mehdizadeh
*Assistant Examiner* — Caitlin R McCleary
(74) *Attorney, Agent, or Firm* — Christopher G. Darrow; Darrow Mustafa PC

(57) ABSTRACT

A storage system for implementing crowdsourced delivery of a parcel can include a communication system configured to communicate wirelessly with an external server to receive an access setting, a storage locker, secured by a primary electronic locking mechanism, including a plurality of inner compartments each secured by respective secondary electronic locking mechanisms, one or more processors, and a memory communicably coupled to the one or more processors and storing: a locking module including instructions that when executed by the one or more processors cause the one or more processors to set the primary electronic locking mechanism and at least one secondary electronic locking mechanism to open in response, respectively, to a primary code and a secondary code based at least in part on information received in the access setting.

20 Claims, 8 Drawing Sheets

(51) Int. Cl.

| | | |
|---|---|---|
| *A61L 2/10* | (2006.01) | |
| *A61L 2/26* | (2006.01) | |
| *B60H 1/00* | (2006.01) | |
| *B60Q 3/30* | (2017.01) | |
| *B60R 9/06* | (2006.01) | |
| *B60R 16/033* | (2006.01) | |
| *B60R 25/01* | (2013.01) | |
| *B60R 25/40* | (2013.01) | |
| *E05B 83/18* | (2014.01) | |
| *G01K 13/00* | (2021.01) | |
| *G06F 16/2455* | (2019.01) | |
| *G06K 7/10* | (2006.01) | |
| *G06Q 10/0631* | (2023.01) | |
| *G06Q 10/0639* | (2023.01) | |
| *G06Q 10/0832* | (2023.01) | |
| *G06Q 10/0835* | (2023.01) | |
| *G06Q 10/0836* | (2023.01) | |
| *G06Q 30/0204* | (2023.01) | |
| *G06Q 30/0207* | (2023.01) | |
| *G06Q 30/0226* | (2023.01) | |
| *G07C 9/00* | (2020.01) | |
| *A23B 2/53* | (2025.01) | |
| *B60P 3/04* | (2006.01) | |
| *B60P 3/20* | (2006.01) | |
| *G06Q 10/0833* | (2023.01) | |
| *G06Q 50/04* | (2012.01) | |

(52) U.S. Cl.
CPC ........... *B60H 1/00735* (2013.01); *B60Q 3/30* (2017.02); *B60R 9/065* (2013.01); *B60R 16/033* (2013.01); *B60R 25/01* (2013.01); *B60R 25/403* (2013.01); *E05B 83/18* (2013.01); *G01K 13/00* (2013.01); *G06F 16/24558* (2019.01); *G06K 7/10297* (2013.01); *G06Q 10/063114* (2013.01); *G06Q 10/06312* (2013.01); *G06Q 10/06315* (2013.01); *G06Q 10/06398* (2013.01); *G06Q 10/0832* (2013.01); *G06Q 10/08355* (2013.01); *G06Q 10/0836* (2013.01); *G06Q 30/0205* (2013.01); *G06Q 30/0215* (2013.01); *G06Q 30/0226* (2013.01); *G07C 9/00571* (2013.01); *A23B 2/53* (2025.01); *A23V 2002/00* (2013.01); *A61L 2202/11* (2013.01); *A61L 2202/121* (2013.01); *A61L 2202/122* (2013.01); *A61L 2202/14* (2013.01); *A61L 2202/23* (2013.01); *B60P 3/04* (2013.01); *B60P 3/205* (2013.01); *G06Q 10/0833* (2013.01); *G06Q 50/04* (2013.01)

(58) Field of Classification Search
CPC . A61L 2/0047; A61L 2/10; A61L 2/26; A61L 2202/11; A61L 2202/121; A61L 2202/122; A61L 2202/14; A61L 2202/23; B60H 1/00735; E05B 83/18; G01K 13/00; G06Q 10/0832; A23L 3/28; A23V 2002/00; B60P 3/04; B60P 3/205
See application file for complete search history.

(56) References Cited

U.S. PATENT DOCUMENTS

| | | |
|---|---|---|
| 5,501,384 A | 3/1996 | Wisniewski |
| 5,505,358 A | 4/1996 | Haase |
| 5,667,116 A | 9/1997 | Reinhart et al. |
| 5,900,823 A | 5/1999 | Coll-Cuchi |
| 6,149,040 A | 11/2000 | Walker |
| 6,300,873 B1 | 10/2001 | Kucharczyk et al. |
| 6,375,070 B1 | 4/2002 | Snoke |
| 6,997,497 B2 | 2/2006 | Sagi et al. |
| 7,005,982 B1 | 2/2006 | Frank |
| 7,183,903 B2 | 2/2007 | Nicolson et al. |
| 7,225,983 B2 | 6/2007 | Park et al. |
| 7,556,957 B2 | 7/2009 | Rottier et al. |
| 7,627,422 B2 | 12/2009 | Adamczyk et al. |
| 7,699,372 B2 | 4/2010 | Adams et al. |
| 7,784,501 B2 | 8/2010 | Gershtein et al. |
| 7,941,267 B2 | 5/2011 | Adamczyk et al. |
| 8,554,605 B2 | 10/2013 | Oleson et al. |
| 8,909,475 B2 | 12/2014 | Gishen |
| 9,150,158 B2 | 10/2015 | Reiher |
| 9,193,306 B2 | 11/2015 | Espig |
| 9,227,570 B2 | 1/2016 | Fleet, Sr. |
| 9,721,224 B2 | 8/2017 | Waris et al. |
| 9,738,125 B1 * | 8/2017 | Brickley ................. B60D 1/62 |
| 9,813,510 B1 | 11/2017 | Nickels et al. |
| 9,821,768 B2 | 11/2017 | Oz et al. |
| 9,858,737 B2 | 1/2018 | Davidsson et al. |
| 9,902,329 B2 | 2/2018 | Izydorek |
| 9,939,279 B2 | 4/2018 | Pan et al. |
| 10,052,396 B2 | 8/2018 | Salter et al. |
| 10,067,988 B2 | 9/2018 | Choksi et al. |
| 10,124,852 B2 | 11/2018 | Potticary et al. |
| 10,133,995 B1 | 11/2018 | Reiss et al. |
| 10,176,448 B1 | 1/2019 | Rhodes et al. |
| 10,181,111 B1 | 1/2019 | Kohli et al. |
| 10,190,358 B2 | 1/2019 | Makke et al. |
| 10,286,853 B1 | 5/2019 | Carbone et al. |
| 10,318,914 B1 | 6/2019 | Arora et al. |
| 10,319,053 B1 | 6/2019 | Kohli |
| 10,346,784 B1 | 7/2019 | Powell et al. |
| 10,380,535 B1 | 8/2019 | Arora et al. |
| 10,387,824 B2 | 8/2019 | Gillen et al. |
| 10,460,282 B2 | 10/2019 | Stark et al. |
| 10,467,554 B2 | 11/2019 | Yoo et al. |
| 10,467,562 B1 | 11/2019 | Mo et al. |
| 10,565,543 B1 | 2/2020 | Mo et al. |
| 10,583,785 B1 | 3/2020 | Bulcher et al. |
| 10,829,962 B2 | 11/2020 | Ruth et al. |
| 10,916,079 B2 * | 2/2021 | O'Toole ................. H04W 12/64 |
| 11,596,263 B1 * | 3/2023 | Siann ................. A61L 2/07 |
| 2002/0116289 A1 | 8/2002 | Yang |
| 2002/0178016 A1 | 11/2002 | McLellan |
| 2008/0004794 A1 | 1/2008 | Horvitz |
| 2010/0265068 A1 | 10/2010 | Brackmann et al. |
| 2011/0313820 A1 | 12/2011 | Biewald et al. |
| 2012/0029978 A1 | 2/2012 | Olding et al. |
| 2012/0173448 A1 | 7/2012 | Rademaker |
| 2012/0284090 A1 | 11/2012 | Marins et al. |
| 2013/0073428 A1 | 3/2013 | Thramann |
| 2014/0258167 A1 * | 9/2014 | Rohmann ......... G06Q 10/08345 705/335 |
| 2015/0007619 A1 | 1/2015 | Finney et al. |
| 2015/0106292 A1 | 4/2015 | Robinson et al. |
| 2015/0161563 A1 | 6/2015 | Mehrabi |
| 2015/0161564 A1 | 6/2015 | Sweeny et al. |
| 2015/0206093 A1 | 7/2015 | Trew et al. |
| 2015/0242811 A1 | 8/2015 | Gillen et al. |
| 2015/0269521 A1 | 9/2015 | Knapp et al. |
| 2015/0294265 A1 | 10/2015 | Monteverde |
| 2015/0324725 A1 | 11/2015 | Roesbery et al. |
| 2015/0337562 A1 * | 11/2015 | Bacarella ................. G07C 9/30 109/38 |
| 2016/0104112 A1 | 4/2016 | Gorlin |
| 2016/0232487 A1 | 8/2016 | Yonker |
| 2016/0314429 A1 | 10/2016 | Gillen et al. |
| 2016/0364678 A1 | 12/2016 | Cao |
| 2017/0011324 A1 | 1/2017 | Truong et al. |
| 2017/0058348 A1 | 3/2017 | Stuhlmüller et al. |
| 2017/0085948 A1 | 3/2017 | Kang et al. |
| 2017/0124510 A1 * | 5/2017 | Caterino ............... A47G 29/141 |
| 2017/0154303 A1 | 6/2017 | Stark et al. |
| 2017/0193625 A1 | 7/2017 | Fan et al. |
| 2017/0236088 A1 | 8/2017 | Rao |
| 2017/0249581 A1 | 8/2017 | Hens et al. |
| 2017/0337510 A1 | 11/2017 | Shroff et al. |
| 2018/0028124 A1 | 2/2018 | Al-Ali et al. |
| 2018/0061157 A1 * | 3/2018 | Zielkowski ............ A45C 13/20 |

(56) References Cited

U.S. PATENT DOCUMENTS

| | | |
|---|---|---|
| 2018/0165638 A1 | 6/2018 | Wilkinson et al. |
| 2018/0174449 A1 | 6/2018 | Nguyen |
| 2018/0196479 A1 | 7/2018 | Li et al. |
| 2018/0240067 A1 | 8/2018 | Oz et al. |
| 2018/0240128 A1 | 8/2018 | Lu et al. |
| 2018/0315319 A1 | 11/2018 | Spector et al. |
| 2018/0374181 A1 | 12/2018 | Zhang |
| 2019/0003843 A1 | 1/2019 | Pan et al. |
| 2019/0049995 A1 | 2/2019 | Ferguson et al. |
| 2019/0066418 A1 | 2/2019 | Fabre |
| 2019/0084485 A1 | 3/2019 | Rivas Franco et al. |
| 2019/0112119 A1 | 4/2019 | Alexander et al. |
| 2019/0164113 A1 | 5/2019 | Fosgard |
| 2019/0188636 A1 | 6/2019 | Endo et al. |
| 2019/0196479 A1 | 6/2019 | Kaneko et al. |
| 2019/0197470 A1 | 6/2019 | Endo et al. |
| 2019/0206163 A1 | 7/2019 | Sakurada et al. |
| 2019/0220811 A1 | 7/2019 | Naito et al. |
| 2019/0220812 A1 | 7/2019 | Kanaoka et al. |
| 2019/0244318 A1 | 8/2019 | Rajcok et al. |
| 2019/0244460 A1* | 8/2019 | Kaneko ............... G06Q 10/0833 |
| 2019/0250636 A1 | 8/2019 | Szubbocsev |
| 2019/0287063 A1* | 9/2019 | Skaaksrud ............... G06F 21/31 |
| 2019/0378080 A1 | 12/2019 | Srinivasan et al. |
| 2019/0392370 A1 | 12/2019 | Kashi et al. |
| 2019/0392389 A1 | 12/2019 | Gillen et al. |
| 2020/0074396 A1 | 3/2020 | Boccuccia et al. |
| 2020/0165861 A1* | 5/2020 | Bruno ..................... E05B 65/52 |
| 2020/0218281 A1* | 7/2020 | Ono ..................... G06Q 10/0833 |
| 2020/0334987 A1 | 10/2020 | Shoval et al. |
| 2020/0380467 A1 | 12/2020 | Chen |
| 2020/0394746 A1 | 12/2020 | Krishnamurthy et al. |
| 2021/0090020 A1* | 3/2021 | Young ............... G06Q 10/0832 |
| 2021/0097481 A1* | 4/2021 | Salter ..................... A61L 2/088 |
| 2021/0140777 A1 | 5/2021 | Balva |
| 2021/0158288 A1 | 5/2021 | Lee et al. |
| 2021/0370869 A1* | 12/2021 | Tazume ............... G06Q 10/0832 |
| 2021/0394712 A1* | 12/2021 | Blömer ................... E05B 85/26 |
| 2022/0027848 A1 | 1/2022 | Kashi et al. |
| 2022/0229442 A9 | 7/2022 | Shoval et al. |
| 2024/0069567 A1* | 2/2024 | Ono ..................... G05D 1/0276 |

FOREIGN PATENT DOCUMENTS

| | | |
|---|---|---|
| CN | 209075569 U | 7/2019 |
| CN | 110232552 A | 9/2019 |
| EP | 3496052 A1 | 6/2019 |
| GB | 231278 A | 4/1925 |
| JP | 2006027505 A | 2/2006 |
| JP | 2010076529 A | 4/2010 |
| KR | 102087940 B1 | 3/2020 |
| WO | 2001052163 A1 | 7/2001 |
| WO | 2015149910 A1 | 10/2015 |
| WO | 2016012741 A1 | 1/2016 |

OTHER PUBLICATIONS

Final Office Action for U.S. Appl. No. 16/938,289 mailed on Apr. 13, 2022, 24 pages.
Final Office Action for U.S. Appl. No. 16/938,289 mailed on Feb. 2, 2023, 35 pages.
Non-Final Office Action for U.S. Appl. No. 16/938,289 mailed on Oct. 27, 2021, 33 pages.
Non-Final Office Action for U.S. Appl. No. 16/938,289 mailed on Aug. 3, 2022, 26 pages.
Non-Final Office Action for U.S. Appl. No. 16/938,289 mailed on Jun. 23, 2023, 37 pages.
Non-Final Office Action for U.S. Appl. No. 16/938,289 mailed on Feb. 1, 2024, 32 pages.
Final Office Action for U.S. Appl. No. 16/938,289 mailed on May 17, 2024, 35 pages.
Non-Final Office Action for U.S. Appl. No. 16/938,289 mailed on Sep. 24, 2024, 29 pages.
Final Office Action for U.S. Appl. No. 16/938,289 mailed on Dec. 19, 2024, 31 pages.

* cited by examiner

FIG. 7
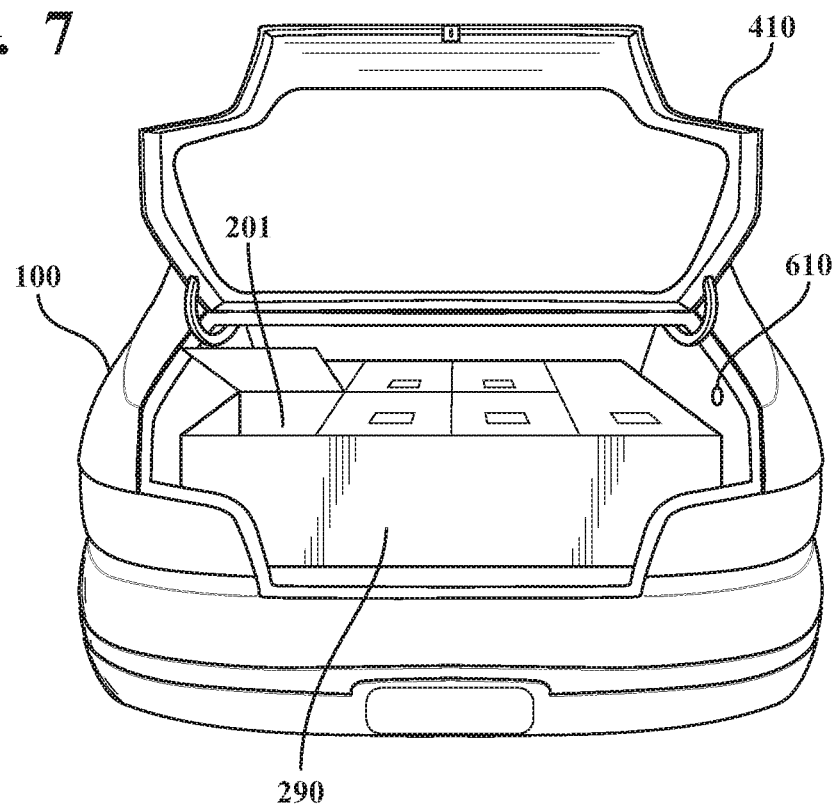
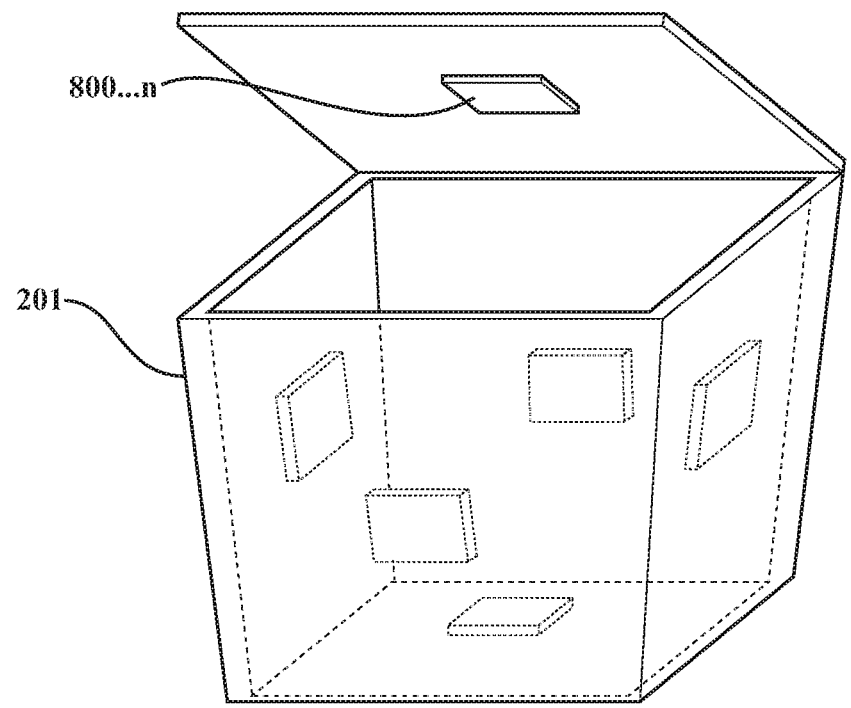
FIG. 8

VEHICLE SYSTEMS FOR DYNAMIC CROWDSOURCED DELIVERY

CROSS-REFERENCE TO PRIORITY APPLICATION

This application claims priority to U.S. Provisional Patent Application No. 63/001,220, filed Mar. 27, 2020, which is commonly assigned herewith and the contents of which are incorporated herein in entirety by reference, with priority claimed for all commonly disclosed subject matter.

TECHNICAL FIELD

The subject matter described herein relates, in general, to delivering goods from place to place, and, more particularly, to storage systems designed for crowdsourced delivery of goods.

BACKGROUND

Retailers, whether on-line or local, are constantly looking for faster and more efficient ways to deliver their products to consumers. Traditionally, the bulk of such deliveries has been handled by major common carriers such as the United States Postal Service (USPS), United Parcel Service (UPS), FedEx, etc. Vehicles that are owned by individuals or entities (e.g., businesses, restaurants, etc.) who use them to travel from place to place and are not employed by a common carrier represent a large untapped resource for carrying parcels from a starting point (e.g., a retail store or a warehouse) to a consumer.

SUMMARY

Example storage systems are disclosed for implementing crowdsourced delivery of goods. In one approach, the disclosed embodiments can operate within a flexible and dynamic crowdsourced delivery service that provides participant vehicles with opportunities to execute deliveries of parcels that meet predefined or user-define delivery criteria, such as preferences regarding conditions about how a parcel should be transported.

In one embodiment, a storage system for implementing a type of crowdsourced delivery of a parcel is disclosed. The storage system can include a communication system configured to communicate wirelessly with an external server to receive an access setting and a delivery setting. The storage system can also include a storage locker that is secured by a primary electronic locking mechanism and includes a plurality of inner compartments, each secured by respective secondary electronic locking mechanisms. One or more sensors can be disposed in each of the plurality of inner compartments.

The system can include one or more processors and a memory communicably coupled to the one or more processors. The memory can store a locking module including instructions that when executed by the one or more processors cause the one or more processors to set the primary electronic locking mechanism and at least one secondary electronic locking mechanism to open in response, respectively, to a primary code and a secondary code based at least in part on information received in the access setting.

The memory can also store a control module including instructions that when executed by the one or more processors cause the one or more processors to detect an aspect of an environment inside at least one of the plurality of inner compartments based at least in part on data from the one or more sensors and to activate one or more environment systems to adjust the environment inside at least one of the plurality of inner compartments based at least in part on the delivery setting.

The memory can further store an interface module including instructions that when executed by the one or more processors cause the one or more processors to communicate with a human-machine interface (HMI) of the vehicle and transmit information associated with the environment of the at least one of the plurality of inner compartments to the HMI, e.g., to be shown on a display within the vehicle.

In another embodiment, a method of controlling a storage system that includes a storage locker secured by a primary electronic locking mechanism and a plurality of inner compartments each secured by respective secondary electronic locking mechanisms includes receiving an access setting and setting the primary electronic locking mechanism and at least one secondary electronic locking mechanism to open in response, respectively, to a primary code and a secondary code based at least in part on information received in the access setting.

The method can further include receiving a delivery setting, detecting an aspect of an environment inside at least one of the plurality of inner compartments based at least in part on data from one or more sensors disposed in the at least one of the plurality of inner compartments, and activating one or more environment systems to adjust the environment based at least in part on the delivery setting.

The method can further include communicating with a human-machine interface (HMI) of the vehicle to transmit information associated with an environment of at least one of the plurality of inner compartments to the HMI.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

FIG. 7 illustrates an example inner compartment open, thereby providing access for an individual to place or remove a parcel for transportation and/or storage purposes, according to the disclosed embodiments.

FIG. 8 illustrates an example inner compartment equipped with one or more ultraviolet (UV) light sanitizing apparatuses, according to the disclosed embodiments.

DETAILED DESCRIPTION

Figure 1:
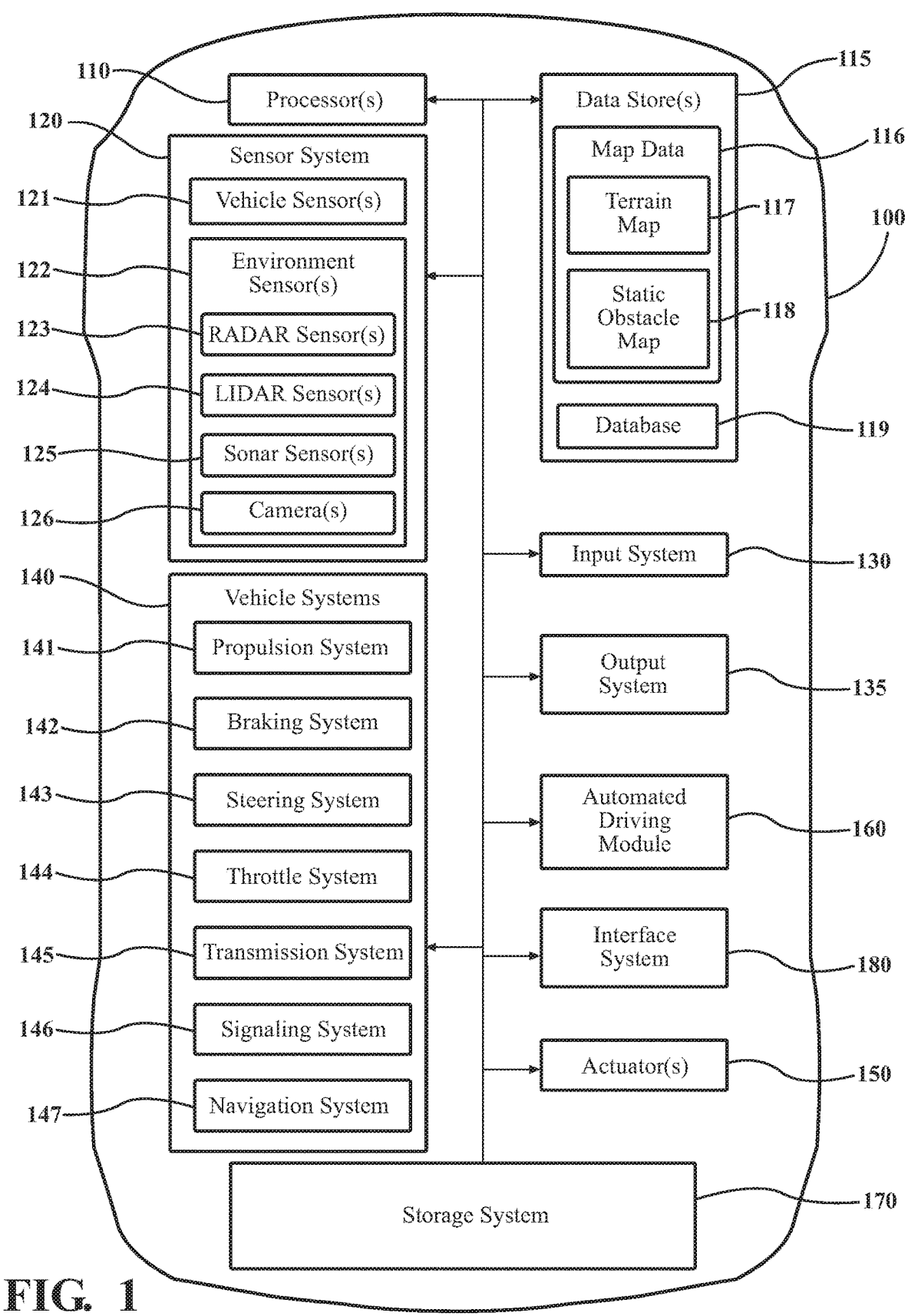
FIG. 1 illustrates one embodiment of a vehicle within which systems and methods disclosed herein may be implemented.

In various embodiments described herein, a storage system, e.g., integrated in a vehicle by a vehicle manufacturer or mounted on a vehicle as an aftermarket accessory, fills a critical role in a crowdsourced parcel delivery system. The crowdsourced parcel delivery system can provide a service through which a parcel may be carried for at least a portion of its delivery route by one or more participants who are willing to carry or store parcels in exchange for some kind of compensation (e.g., reward points or money). Crowdsourced shipping can be applied to the so-called "middle mile" between the retail store or warehouse and a hub (e.g., a distribution center) relatively close to the destination, to the so-called "last mile" from that final hub to the destination, or both.

A vehicle manufacturer is uniquely positioned to tap its large customer base (e.g., owners of the vehicles it manufactures and sells) to facilitate crowdsourced delivery of parcels and other items to consumers. For example, a vehicle manufacturer can design and construct a vehicle to include an integrated storage system as disclosed herein or design vehicle systems prepared to cooperate with aftermarket products and modifications that enable the vehicle to participate in crowdsourced shipping as described herein. Such designs can include the use of intelligent hardware and software systems, e.g., a mobile app for drivers (participants) to use for managing storage conditions and handoffs between crowdsourced drivers as a parcel is transported.

Throughout this description, the term "parcel" refers to an item, including products, food, living things such as animals or plants, etc., or another object that is transported from a point of origin (e.g., store or warehouse) to a destination (e.g., a residence or place of business). Also, for the purposes of this description, a "consumer" is a person who purchases an item, e.g., from an on-line or local retailer, and who specifies the location to which the item should be delivered. The term "user," as in a user of the crowdsourced delivery system, is sometimes used interchangeably with "consumer." Herein, a "common carrier" refers to a commercial delivery service, such as USPS, UPS, FedEx, etc., that a user may engage with as a delivery service, sometimes in conjunction with a crowdsourced parcel delivery service.

Herein, a "participant" is a person who owns and/or operates a vehicle having a type storage system as disclosed herein and participates in the disclosed crowdsourced parcel delivery operation by storing and/or transporting a parcel in the storage system in accordance with parameters determined by the crowdsourced parcel delivery system. The term "driver" is sometimes used interchangeably with "participant."

The term "vehicle" herein refers to any form of motorized transport, such as a pod, an automobile, e.g., a hybrid/electric automobile, an autonomous/semi-autonomous automobile, a combination thereof, etc. While arrangements will be described herein with respect to automobiles, it will be understood that embodiments are not limited to automobiles.

FIG. 1 illustrates an example of a vehicle 100. As shown in FIG. 1, the vehicle 100 includes multiple elements. It will be understood that in various embodiments it may not be necessary for the vehicle 100 to have all of the elements shown in FIG. 1. The vehicle 100 can have any combination of the various elements shown in FIG. 1. Further, the vehicle 100 can have additional elements to those shown in FIG. 1. In some arrangements, the vehicle 100 may be implemented without one or more of the elements shown in FIG. 1. While the various elements are shown as being located within the vehicle 100 in FIG. 1, it will be understood that one or more of these elements can be located external to the vehicle 100. Further, the elements shown may be physically separated by large distances.

Some of the possible elements of the vehicle 100 are shown in FIG. 1 and will be described along with subsequent figures. However, a more detailed description of many of the elements in FIG. 1 will be provided after the discussion of FIGS. 2-11 for purposes of brevity in this description. It will be appreciated that for simplicity and clarity of illustration, where appropriate, reference numerals have been repeated among the different figures to indicate corresponding or analogous elements. In addition, while the discussion outlines numerous specific details to provide a thorough understanding of the embodiments described herein, those of skill in the art will understand that the embodiments described herein may be practiced using various combinations of these elements.

In any case, the vehicle 100 includes a storage system 170 that is implemented to perform methods and other functions as disclosed herein relating to holding parcels for storage and/or transportation purposes in accordance with one or more delivery parameters received from a user. The noted functions and methods will become more apparent in the following discussion of the figures.

In one embodiment, the storage system 170 is operably connected with a user interface system 180, which can be implemented as a human machine interface (HMI). The user interface system 180 can include, for example, one or more dashboard screens, a touch screen, an infotainment screen, a windshield screen or other type of vehicle user interface.

Figure 2:
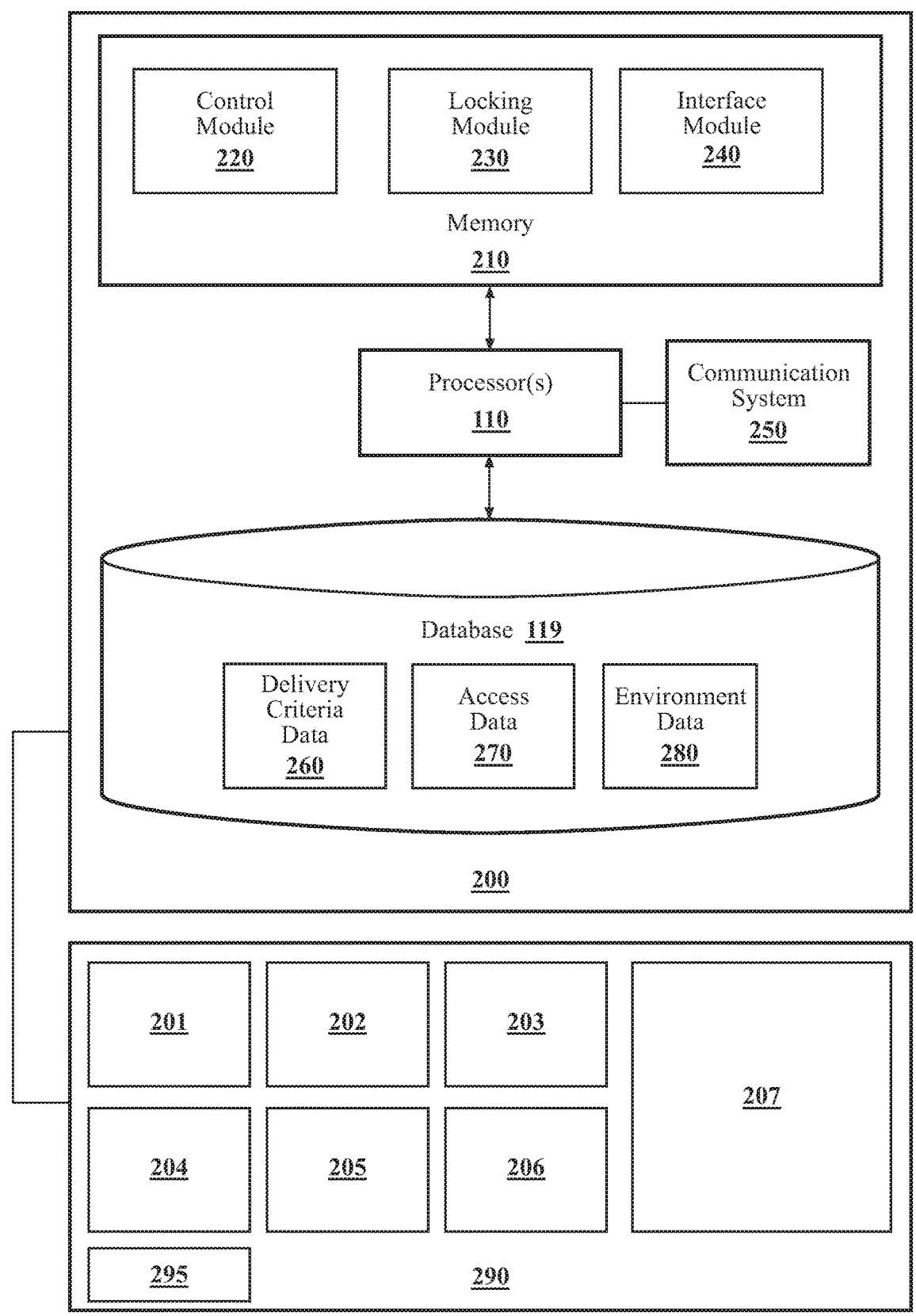
FIG. 2 illustrates one embodiment of a storage system according to the disclosed embodiments.

FIG. 2 illustrates one embodiment of the storage system 170 of FIG. 1. The storage system 170 is shown as including a control unit 200 communicably connected to a storage unit 290. The storage unit 290 includes a plurality of inner compartments 201-207 that may vary in size, shape and feature set, as will be discussed further below.

The storage unit 290 can be implemented, for example, as a storage housing or locker within an interior space of the vehicle 100, such as a trunk, or installed on an exterior space, such as a truck bed or roof. The storage unit 290 can be secured by a primary locking mechanism 295, which can be implemented as an electronic locking mechanism that can be controlled, e.g., locked or unlocked, in response to a signal received from the control unit 200.

In one or more embodiments, the storage unit 290 is disposed inside a trunk of the vehicle 100 and the primary locking mechanism 295 controls access to the trunk. In one or more embodiments, the storage unit 290 is installed outside of the trunk, e.g., on top of the vehicle 100 or in a truck bed of the vehicle 100, and the primary locking mechanism 295 controls access to the storage unit 290 itself, e.g., to a lid or door of the storage unit 290. The primary locking mechanism 295 can include an input device, for example, a touch screen, a keypad, a camera, a card reader, a bio-scanner, a chip reader, a near-field communication (NFC) reader, a wireless communication device or another type of input device that can be configured to allow a user to input a code or credential that causes the primary locking mechanism 295 to unlock and allow access to the storage unit 290.

Inside the storage unit 290, one or more of the inner compartments 201-207 can be individually labeled with an identifier and secured by respective secondary locking mechanisms (not shown). One or more of the inner compartments 201-207 may also include one or more types of sensors (not shown), input devices (not shown), sanitizing systems (not shown), and/or environment control systems (not shown), as will be discussed further below.

The control unit 200 is communicatively connected to the storage unit 290 and includes a processor 110 and database 119 from the vehicle 100 of FIG. 1. The processor 110 may be part of the storage system 170, the storage system 170 may include a processor separate from the processor 110 of the vehicle 100, or the storage system 170 may access the processor 110 through a data bus or another communication path as shown in FIG. 1.

The control unit 200, in one embodiment, includes a memory 210 that stores a control module 220, a locking module 230, and an interface module 240. The memory 210 can be constructed as a random-access memory (RAM), a read-only memory (ROM), a hard-disk drive, a flash memory, or another suitable memory for storing the modules 220, 230, and 240. The modules 220, 230, and 240 are, for example, constructed as computer-readable instructions that when executed by the processor 110 cause the processor 110 to perform the various functions disclosed herein.

The storage system 170 can also include a communication system 250 that allows the storage system 170 to receive delivery criteria data and access data, and to communicate, for example, with communication networks, server systems, mobile computing devices, and other systems, such as a server implementing a crowdsourced parcel delivery system. The communication system 250 can be implemented, for example, as a wireless communication system including one or more transmitting/receiving devices, one or more transmitting/receiving antennas and a controller for transmitting and receiving data over a wireless network using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi™), Wi-Fi™ Direct, 802.16 (WiMAX), ultra-wideband (UWB), Wibree, and/or any other wireless protocol. The communication system 250 can be configured to securely communicate wirelessly with an external server, such as, a crowdsourced parcel delivery service, to transmit status information and receive delivery instructions. In one or more embodiments, the delivery instructions can include a delivery setting that indicates how a parcel should be transported by the storage system 170 and an access setting that indicates how a parcel should be secured by the storage system 170.

The storage system 170 can further include a database 119 that stores, among other things, delivery criteria data 260, access data 270 and environment data 280, which will each be described further below. The database 119, in one embodiment, is constructed as an electronic data structure stored in the memory 210 or another data store, such as the vehicle 100 data store 115, a cloud-based storage, a removable memory device, or another suitable location that is accessible to the modules 220, 230, and 240. The database 119 is configured with routines that can be executed by the processor 110 for analyzing stored data, providing stored data, organizing stored data, and so on. Thus, in one embodiment, the database 119 stores data described above (as well as other data) used by the modules 220, 230, and 240 in executing various functions.

The control module 220 generally includes instructions that function to control the processor 110 to detect an environment inside at least one of the inner compartments 201-207 based at least in part on data from one or more sensors in or around the inner compartments 201-207, and to activate one or more environment systems to adjust the environment based at least in part on information received in the delivery setting. In one or more embodiments, the control module 220 can further include instructions to detect a status (e.g., empty, not empty) of at least one of the inner compartments 201-207 based at least in part on the data from one or more sensors and report the status to an external system, e.g., a crowdsourced parcel delivery system. That is, for example, an automated crowdsourced parcel delivery system can directly query the storage system to request information regarding which, if any, inner compartments 201-207 are available for use and what additional features (as discussed below) the inner compartments 201-207 have.

The locking module 230 generally includes instructions that function to control the processor 110 to set the primary electronic locking mechanism 295 and at least one secondary electronic locking mechanism to open in response to respective codes based at least in part on information received in the access setting. In this manner, for example, a crowdsourced parcel delivery system in communication with the storage system 170 can remotely manage who has access to a parcel within the storage system 170 by managing distribution of access codes. Furthermore, in one or more embodiments the parcel can be delivered inside a secure container locked with a tertiary locking mechanism, and the locking module 230 can further include instructions to set the tertiary locking mechanism to unlock in response to a tertiary code determined based at least in part on information received in the access setting, thereby providing a third layer of security.

The interface module 240 generally includes instructions that function to control the processer 110 to communicate with a human-machine interface (HMI) of the vehicle (e.g., interface system 180 of FIG. 1) and transmit information associated with an environment of at least one of the inner compartments 201-207 to the HMI. For example, the interface module 240 can be configured to display a menu on a user interface of the vehicle 100 that allows a driver of the vehicle 100 to selectively see information regarding the status and/or features of one or more of the inner compartments 201-207. The information can include, for example, one or more of a temperature level, a battery power level, an inner view, and a humidity level associated with at least one of the inner compartments 201-207.

In one or more embodiments, the interface module 240 further includes instructions to control a climate control system to adjust a temperature inside the at least one of the inner compartments 201-207 based on a command received from the HMI. This can allow, for example, a driver of the vehicle 100 to control systems that effect the environment in one or more of the inner compartments 201-207 via the vehicle HMI. In one or more embodiments, the interface module 240 can include communication protocol instructions to further extend functionality to a mobile device, such as via a phone or a tablet app that is configured to communicate with the interface module 240, thereby allowing a driver to have mobile access to information and controls regarding the inner compartments 201-207.

Figure 3:
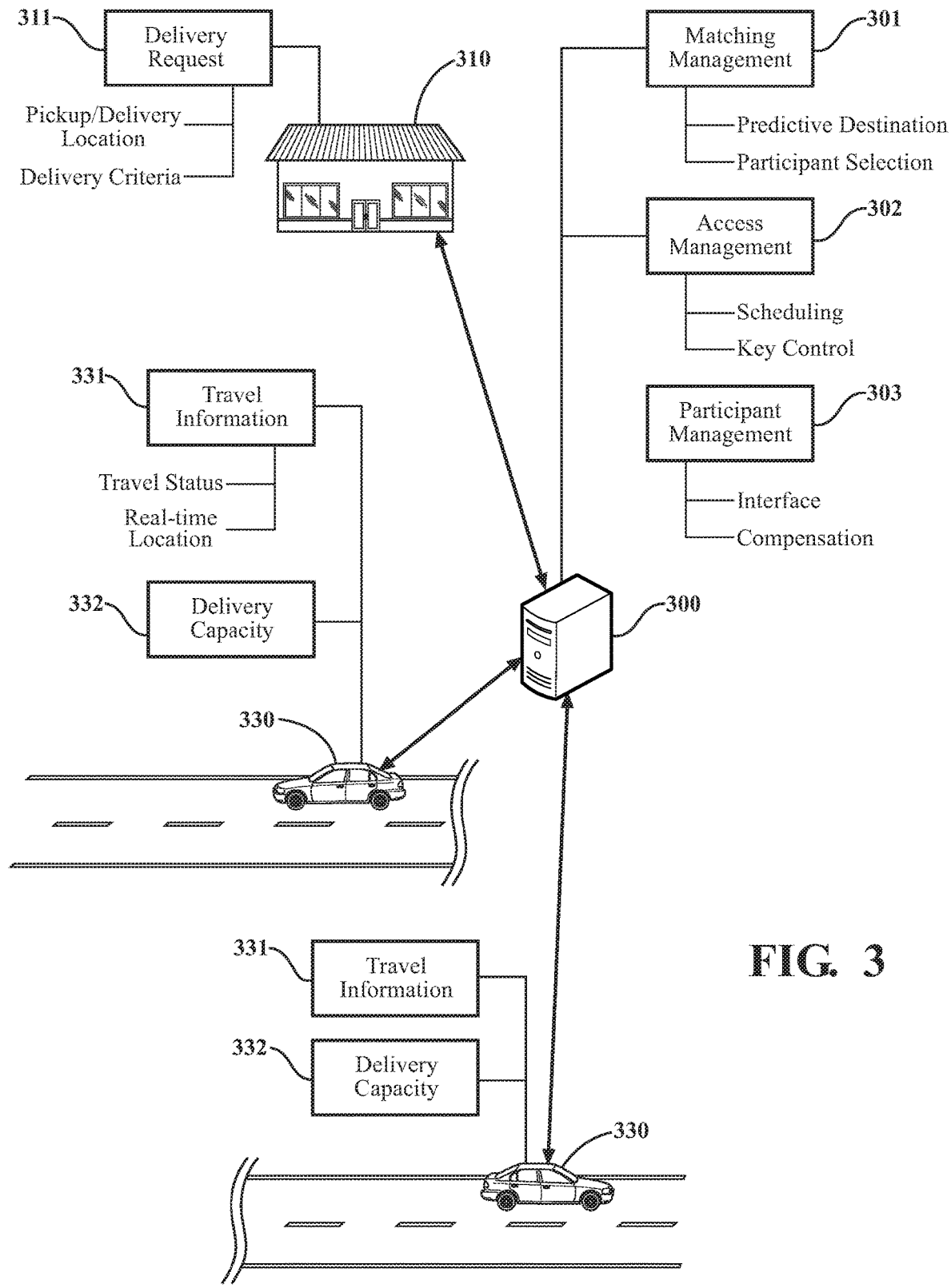
FIG. 3 illustrates a general overview of an example crowdsourced parcel delivery system as an example context in which the disclosed storage system can operate, according to the disclosed embodiments.

FIG. 3 illustrates a general overview of an example crowdsourced parcel delivery system 300 which is an example context in which the disclosed storage system 170 can operate, according to the disclosed embodiments. The crowdsourced parcel delivery system 300 may be implemented, for example, as one or more cloud/edge computing devices, a server, or another network connected computing device capable of storing data, executing instructions and communicating with multiple entities in carrying out the functions described herein. In one or more embodiments, the crowdsourced parcel delivery system 300 can be operated by a vehicle manufacturer that produces vehicles having features of the storage system 170 specifically designed to operate with the system 300, but the disclosed embodiments are not limited to this type of entity operating the disclosed system. Other entities may also implement the disclosed embodiments in different ways, for example, through aftermarket modifications and other products.

As shown in FIG. 3, the example crowdsourced parcel delivery system 300 can receive a delivery request 311 from a user, e.g., a retailer 310. The delivery request 311 can include various types of information, including pickup/drop-off locations and delivery criteria, such as transport preferences (e.g., refrigerator, heated, ventilated, etc.), timing preferences, alternate drop-off locations, etc. In response to the delivery request 311, the crowdsourced parcel delivery system 300 can analyze a network of participants 330 to automatically identify, select, and manage a plurality of participants 330 to complete the delivery request 311 according to the delivery criteria, including managing aspects of the disclosed storage system 170 to meet delivery route requirements.

At an operational level, the crowdsourced parcel delivery system 300 can provide multiple functions that may generally be categorized as matching management 301, access management 302, and participant management 303. The participants 330 provide travel/traffic information and provide storage and/or transportation services by deploying a storage system 170 as disclosed herein.

Storage services and transportation services may be viewed as distinct services provided within the context of the example crowdsourced parcel delivery system 300. For example, as will be discussed further below, a participant 330 may be operating a stationary unit (e.g., a parked vehicle) and provide only storage service (e.g., access to the storage system 170, for example, to facilitate a handoff) or may be operating a mobile unit (e.g., a traveling vehicle) and provide both storage and transportation service.

Continuing the description of FIG. 3, the participants 330 provide the crowdsourced parcel delivery system 300 with information, including travel information 331 and delivery capacity 332, which indicates availability and features of inner compartments of the storage system 170 for a given participant 330. Travel information 331 can include travel status (i.e., currently stationary, upcoming scheduled route, currently moving, etc., as well as information regarding traffic conditions in a vicinity of the participant 330), and real-time location of the participant 330. Providing real-time location enables the crowdsourced parcel delivery system 300 to determine which participant 330 or combination of participants 330, through a series of handoffs along a particular route, are able to fulfill the delivery request 311 and convey the parcel to its ultimate destination or, for example, to a hub from which another carrier (e.g., a common carrier) can perform last-mile delivery.

In one or more embodiments, the crowdsourced parcel delivery system 300 determines real-time location by tracking participants 330 based on the participants 330 reporting GPS coordinates over a network (e.g., cellular data) to the system 300. In other embodiments, the system 300 tracks the real-time location of participants 330 based on receiving a reported location of a mobile computing device (e.g., a smartphone) carried by an owner/driver. In any case, participants 330 agree to tracking terms prior to participating in the crowdsourced parcel delivery system 300, for example, to earn rewards such as points or cash. Real-time tracking of vehicles, in the context of the embodiments described herein, is, therefore, expected and does not result in privacy violation.

As previously stated, in addition to travel information 331 a participant 330 can also inform the crowdsourced parcel delivery system 300 of a delivery capacity 332 of the participant. Delivery capacity 332 can include a report on the availability of a participant 330 to take part in a delivery as well as the availability and features of inner compartments of the storage system 170 deployed by the participant 330.

Referring to the crowdsourced parcel delivery system 300 of FIG. 3, matching management 301 generally handles identifying and selecting participants 330 to convey the parcel while attempting to meet requirements established by delivery criteria included in the delivery request 311. In one or more embodiments, matching management 301 can include a predictive destination function and a participant selection function.

The predictive destination function is configured to intelligently generate predicted travel plans of one or more participants 330 based on historical data that indicates driving habits of the participants 330. The historical data can include, for example, past routes traveled by a given participant, dates and times of the past routes, and a time log of completed deliveries.

The participant selection function selects participants 330 to include in the delivery process based on the predicted travel plans, travel information and delivery capacity obtained from the participants 330, as well as the delivery criteria indicated in the delivery request 311.

Access management 302 includes functions of scheduling (i.e., logistics, drop-off/pickup, transfers, etc.) and generating and/or managing access keys to the storage system 170 as part of the process of facilitating secure movement of a parcel through multiple participants 330 along a delivery route. A delivery route can involve multiple parties and include storage systems 170 deployed in a mixture of stationary hubs (e.g., a parked vehicle, a store, a public locker facility, a participant's place of business, etc.) and mobile hubs (e.g., moving vehicles), depending on the particular embodiment and the particular parcel being shipped. Key control refers to controlling who has access to the parcel as it is transported on a delivery route in various storage systems 170 and at what times such access is permitted.

Participant management 303 includes functions to manage compensation/rewards for participants 330 and software/hardware interfaces between the crowdsourced parcel delivery system 300 and: (1) users, such as nation-wide stores, on-line stores, resellers, small local retailers, individuals, consumers, etc. and (2) participants 330 who participate in the system by storing and/or transporting parcels in the storage system 170.

Regarding the interface with users, the crowdsourced parcel delivery system 300 can include backend communication systems that seamlessly communicate with a retailer's point-of-sale (POS) system such that when a consumer purchases an item from the retailer, the retailer's POS system, in presenting shipping options to the consumer, can include the option of shipment via the crowdsourced parcel delivery system 300 described herein. Regarding the interface with participants 330, the system 300 can include, for example, a website and/or a mobile app (e.g., for smartphones, tablet computers, etc.) for participants 330 to access that allows the crowdsourced parcel delivery system 300 to communicate with the participants 330. For example, the system 300 can send participants 330: invitations (e.g., via text message, app-notification, etc.) to accept delivery tasks, updates regarding handoffs to other participants 330, updates regarding changes to the delivery route, updates regarding earned rewards/compensation, and other communications.

The compensation function of participant management 303 operates to dispense rewards (e.g., monetary rewards, points, etc.) to participants 330 for completing delivery tasks. For example, in one or more embodiments, a participant 330 that repeatedly completes delivery points can earns points that accumulate over time. The points can have an associated value that can be spent or redeemed with a vehicle manufacturer, a retailer, or one or more other entities. In one or more embodiments, the crowdsourced parcel delivery system 300 can dispense rewards in the form of a gift card, a discount on future purchases, or other incentives.

In one or more embodiments, participant management 303 can dispense cash payments (e.g., a direct deposit in a bank account) to participants 330 as compensation. For example, in one or more embodiments, for a given parcel delivery that the user pays a delivery fee to fulfill, the entity implementing the crowdsourced parcel delivery system 300 may receive a percentage of the delivery fee and the participants 330 who provide transportation and/or storage services to convey the parcel may also receive a percentage of the delivery fee.

A participant 330 deploying a storage system 170 as disclosed herein may register an account with the crowdsourced parcel delivery system 300 as a prerequisite for accepting jobs, and the system 300 can in response create a profile for the participant 330. The profile can store, among other things, details regarding features of the storage system 170 (e.g. as discussed below regarding FIGS. 7-10), an identification code, biometric data for access to secure components in execution of a delivery, preferred compensation method and associated information (e.g., direct deposit account information), and communication information (e.g., registered app, vehicle app, cellphone number, etc.) that allow the crowdsourced parcel delivery system 300 to transmit job invitations to the participant 330 and to receive travel information and delivery capacity information from the participant 330. The profile can also be mapped to an associated vehicle by VIN or license plate number.

As shown in FIG. 3, the crowdsourced parcel delivery system 300 can receive a delivery request 311 from a user, for example, a retailer 310. The delivery request 311 can include a description of the parcel to be delivered, a pickup location (e.g., address of the retailer 310), a drop-off location (e.g., address of the consumer that purchased the item being delivered) and delivery criteria (e.g., user preferences specific to each individual delivery).

The crowdsourced parcel delivery system 300 can determine a delivery route that may include one or more handoffs between participants. To facilitate secure transfer of the parcel, each of the participants 330 can operate a vehicle (or in some instances, a facility) that includes the disclosed storage system 170.

The crowdsourced parcel delivery system 300 can generate, for each of the participants 330, access keys that allow access to the storage system 170, the secure compartment and, when applicable, the secure container used to transport the parcel. The access keys can be implemented in any of various ways depending on implementation of the locking mechanisms of the secure storage locker and the inner compartments. For example, in one or more embodiments the access keys can be implemented as an access code to be entered (e.g., via touch screen, keypad, etc.), a code associated with biometric data (i.e., of the drivers) of the participants 330, a code associated with a scannable image transmitted to and displayed on mobile devices belonging to participants 330, a code associated with a wireless signal such as a Bluetooth or near field communication (NFC) signal to be transmitted to and broadcast from mobile devices belonging to participants 330, or another type of access key that can be provided to the participants 330.

The crowdsourced parcel delivery system 300 can dynamically manage timing windows during which the access keys are valid based on a handoff/pickup schedule per route. For example, referring to FIG. 4, in one example scenario the crowdsourced parcel delivery system 300 selects two participants to execute delivery of the parcel. The system 300 can analyze a regional map 415 to determine a first route that proceeds from the pickup location 400 (e.g. a retail store) along segment 420 to a handoff location 425, then proceeds along segment 430 to the delivery destination 410, and a second route that proceeds from the pickup location 400 along segment 440 to a handoff location 445, then proceeds along segment 450 to the delivery destination 410. The system 300 assigns a first participant the delivery tasks of picking up the parcel from the pickup location 400 at 12:00 and transporting the parcel from the pickup location 400 to the handoff location 425 along route segment 420. The system 300 assigns a second participant the delivery tasks of picking up the parcel from the handoff location 425 and transporting the parcel to the delivery destination 410. The handoff location 425 may be, for example, a parking lot at a store or an office building that first participant is traveling to.

The first participant is deploying a storage system 170 (FIG. 2) according to the disclosed embodiments. The crowdsourced parcel delivery system 300 can estimate a time that the first participant should arrive at the handoff location 425 (e.g., 12:15) and estimate a time that the second participant should arrive at the handoff location 425 (e.g., 12:30). Based on the estimated arrivals, the system 300 can generate access keys for the second participant that are valid to access the storage system 170 of the first participant only for a timing window estimated to include both arrivals (e.g., 12:10 to 12:40).

Figure 4:
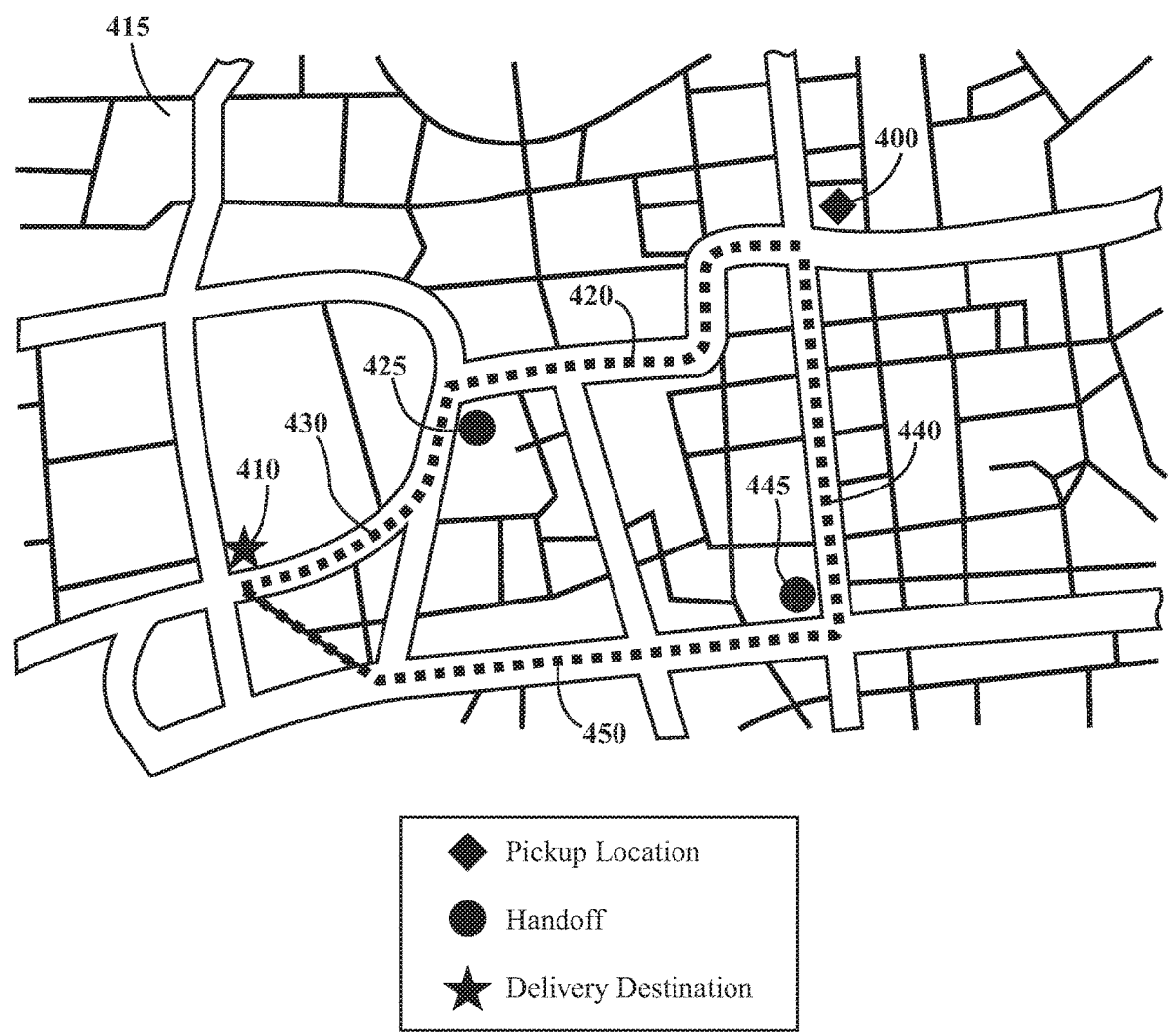
FIG. 4 illustrates an example scenario of a crowdsourced parcel delivery system that selects two participants to execute delivery of a parcel, according to the disclosed embodiments.

Referring to FIGS. 2 and 4, the system 300 can transmit the access keys and the timing of their validity to the storage system 170 of the first participant. The storage system 170 (e.g., locking module 230) can receive and store the access keys and timing information as access data 270. Based on the stored access data 270, the locking module 230 can implement the access window, i.e., set a primary locking mechanism 295 to open based on a first received access key during the timing window, and in one or more embodiments set a secondary locking mechanism for an inner compartment (e.g., 201) as well.

Thus, the first participant can park at the handoff location 425 and leave the vehicle as usual (e.g., enter the store, enter the office building, etc.) without waiting for the second participant. The second participant can utilize the access keys to retrieve the parcel from the storage system 170 of the vehicle at the handoff location 425 during the timing window.

In one or more embodiments, the system 300 can issue access keys to participants on an only as-needed basis. For example, in a three-layer security implementation (i.e., secure storage locker, secure inner compartment, secure container), the system 300 can issue access keys to only the first two layers for a participant that is transporting the parcel between handoff locations and therefore does not need to have access to the secure container.

Figure 5:
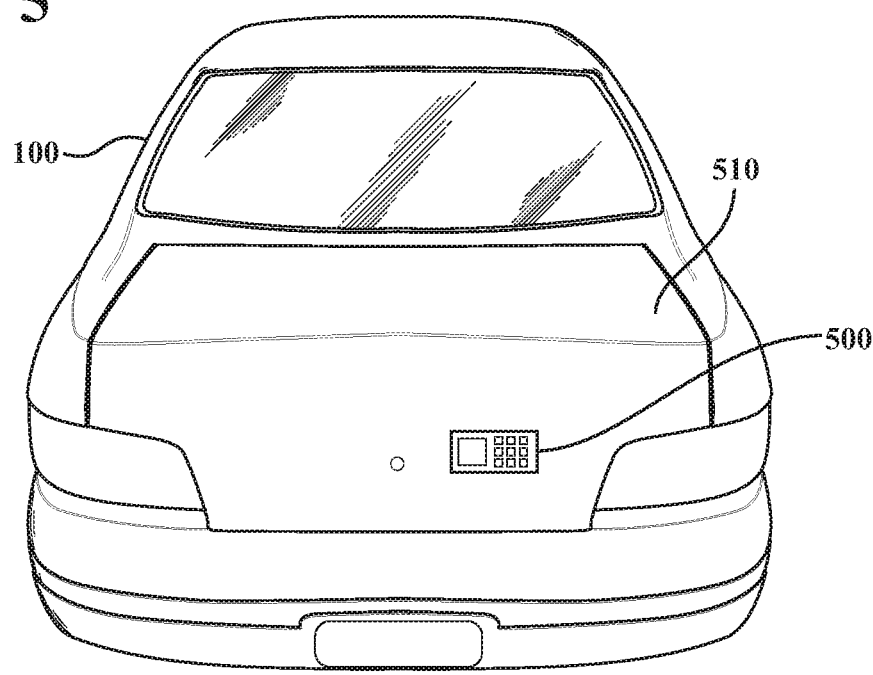
FIG. 5 illustrates an example rear view of a vehicle implementing a secure storage system, according to the disclosed embodiments.

FIG. 5 shows an example rear view of a vehicle 100 implementing a secure storage system 170 according to the disclosed embodiments. In the implementation illustrated, the storage system 170 is disposed within a trunk 510 of the vehicle 100, although in other implementations the storage system 170 may be installed elsewhere on a vehicle outside of a trunk, e.g., on a roof or in a truck bed. In the implementation shown, the storage system 170 includes a security input device 500 accessible on the trunk 510. For example, in one or more embodiments the primary locking mechanism 295 can include an input device, for example, a touch screen, a keypad, a biometric-scanner, a camera, a card reader, a chip reader, a near-field communication (NFC) reader, a wireless communication device or another type of input device that can be configured to allow a user to input a code, an identification or a credential that causes the primary locking mechanism 295 to unlock and gain access to the storage unit 290.

Figure 6:
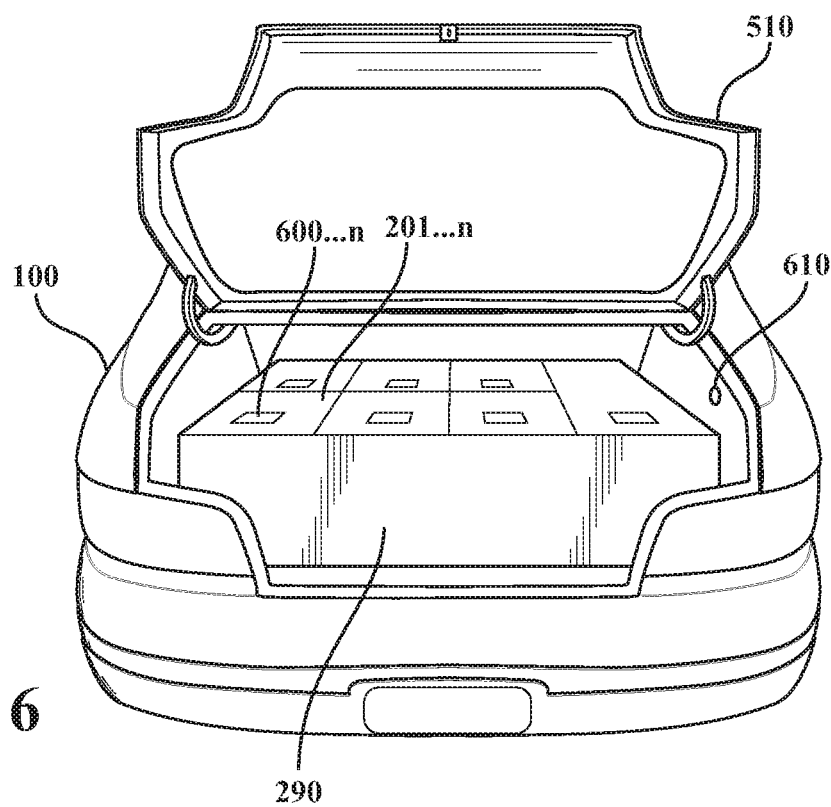
FIG. 6 illustrates an example rear view of a vehicle trunk open showing access to a storage system, according to the disclosed embodiments.

FIG. 6 shows the trunk 510 open, providing access to the storage unit 290, which includes multiple, secured inner compartments 201 . . . n. In one or more embodiments, each of the inner compartments 201 . . . n can be labeled with an associated identifier and can include a secondary locking mechanism (not shown) and an individual input device 600 . . . n, which can be similar to the input device 500 shown in FIG. 5. For example, the secondary locking mechanism of inner compartment 201 can secure a lid of the compartment 201 and be configured to unlock in response to a key signal (e.g., access code, biometric ID, etc.) received via input device 600.

In one or more embodiments, the storage system 170 can include a hidden surveillance camera 610 that captures video of parcels being placed in or removed from the inner compartments 201 . . . n. FIG. 7 shows the inner compartment 201 open, thereby providing access for an individual to place or remove a parcel for transportation and/or storage purposes.

The inner compartments 201 . . . n can individually include one or more different features. To power the features, one or more of the inner compartments 201 . . . n can each be connected to individual batteries that can be charged by the vehicle 100, or can be directly connected to a power system of the vehicle 100 to receive operating power. A few example features will now be discussed.

FIG. 8 illustrates an example inner compartment 201 equipped with one or more ultraviolet (UV) light sanitizing apparatuses 800 . . . n. For example, in one or more embodiments the inner compartment 201 can be equipped with multiple UV light sanitizing apparatuses 800 . . . n arranged to direct ultraviolet light toward at least a top, a bottom and a plurality of sides of a parcel when the parcel is placed inside the inner compartment 201.

Figure 9:
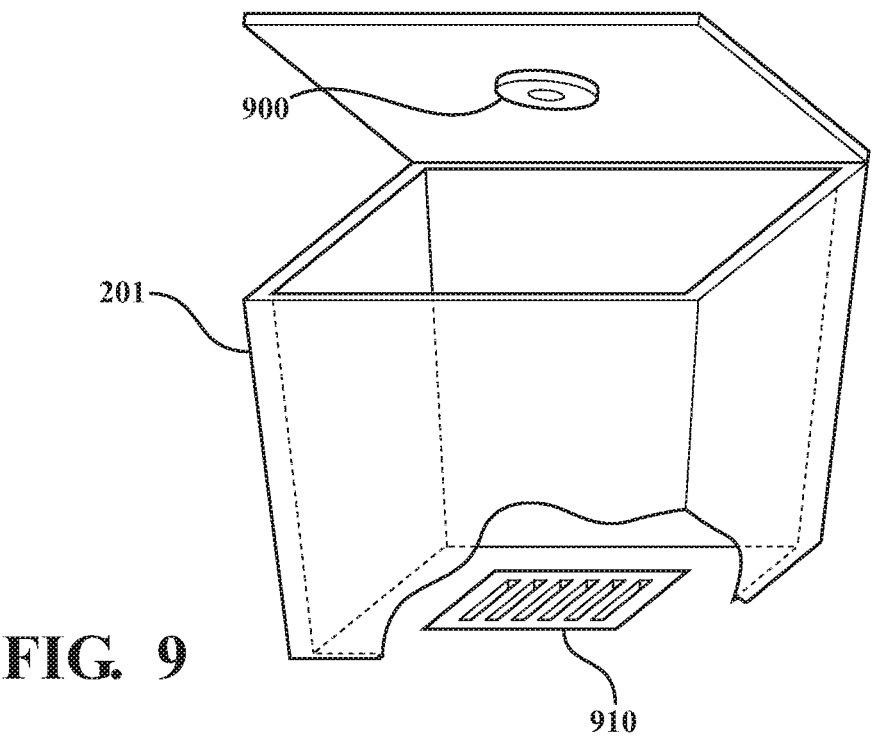
FIG. 9 illustrates an example inner compartment equipped with a climate-controlled ventilation interface, according to the disclosed embodiments.

FIG. 9 illustrates another example feature, climate control, that an example inner compartment 201 may be equipped with. In one or more embodiments, one or more inner compartments 201 . . . n can be individually climate controlled via a ventilation interface 910 connected to the vehicle 100 HVAC system or through a separate climate-control system integrated with the storage unit 290. In one or more embodiments, the climate control feature can include a general ventilation feature to ensure air flow into the inner compartment 201, e.g., for transport of living things such as pets or plants.

The inner compartment 201 can further include one or more sensors 900 that can detect a temperature of an environment inside of the inner compartment 201. In one or more embodiments, the one or more sensors 900 can include a camera, a lidar, or another type of sensor to detect the presence or the absence of a parcel within the inner compartment 201.

Figure 10:
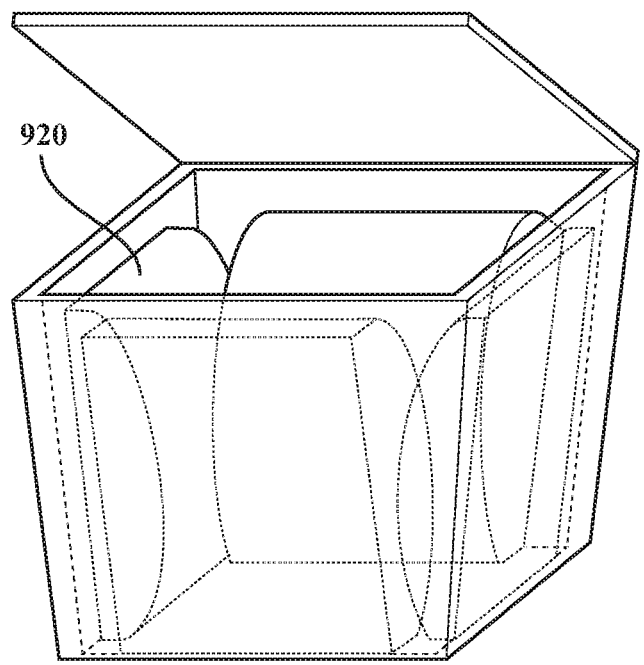
FIG. 10 illustrates an example inner compartment equipped with adjustable protective padding, according to the disclosed embodiments.

FIG. 10 illustrates yet another example feature. In one or more embodiments, one or more of the inner compartments 201 . . . n can be equipped with adjustable protective padding for protecting highly fragile parcels. For example, the walls of an inner compartment 201 can be outfitted with rubber pneumatic bladders 920 whose degree of inflation can be adjusted (e.g., automatically by the control unit 200 or manually by an individual) to accommodate the size of a particular parcel or to provide protection against jostling during transport.

One or more of the inner compartments 201 . . . n can be equipped with one or more of the above-discussed features. In one or more embodiments, various ones of the inner compartments 201 . . . n are equipped with different individual features or combinations of features thereby providing a variety of storage options within the storage unit 290. In one or more embodiments, each of the inner compartments 201 . . . n is equipped with an individual feature or some combination of features.

Furthermore, the concepts associated with the above-described storage unit 290 and inner compartments 201 . . . n can be generalized to other aspects of vehicle access. For example, in one embodiment, the vehicle 100 passenger compartment can be partitioned internally into multiple storage compartments, and each door of the vehicle 100 can be separately secured by a digital lock (e.g., accessible through a perishable digital key supplied by the crowd-sourced parcel delivery system 300, as discussed above) so that a person picking up or dropping off a parcel can open only the permitted door to access only the permitted compartment involving the subject parcel while denying the person access to all other doors and compartments within the vehicle 100.

Also, the information regarding the status or availability of the above-discussed features, such as ultraviolet (UV) light sanitizing, climate control and adjustable padding, can be available to the crowdsourced parcel delivery system 300 (e.g., stored in vehicle profile data) so that, for example, a vehicle with sanitizing capabilities can be selected by the access management function of the system 300 when a purchasing consumer requests that feature or there is another reason (e.g., government regulations) for a sanitizing compartment.

The inner compartments 201 . . . n may have different sizes/shapes and/or different features (e.g., refrigerated, disinfected, warmed, ventilated, etc.) to match different parcel transport needs.

Figure 11:
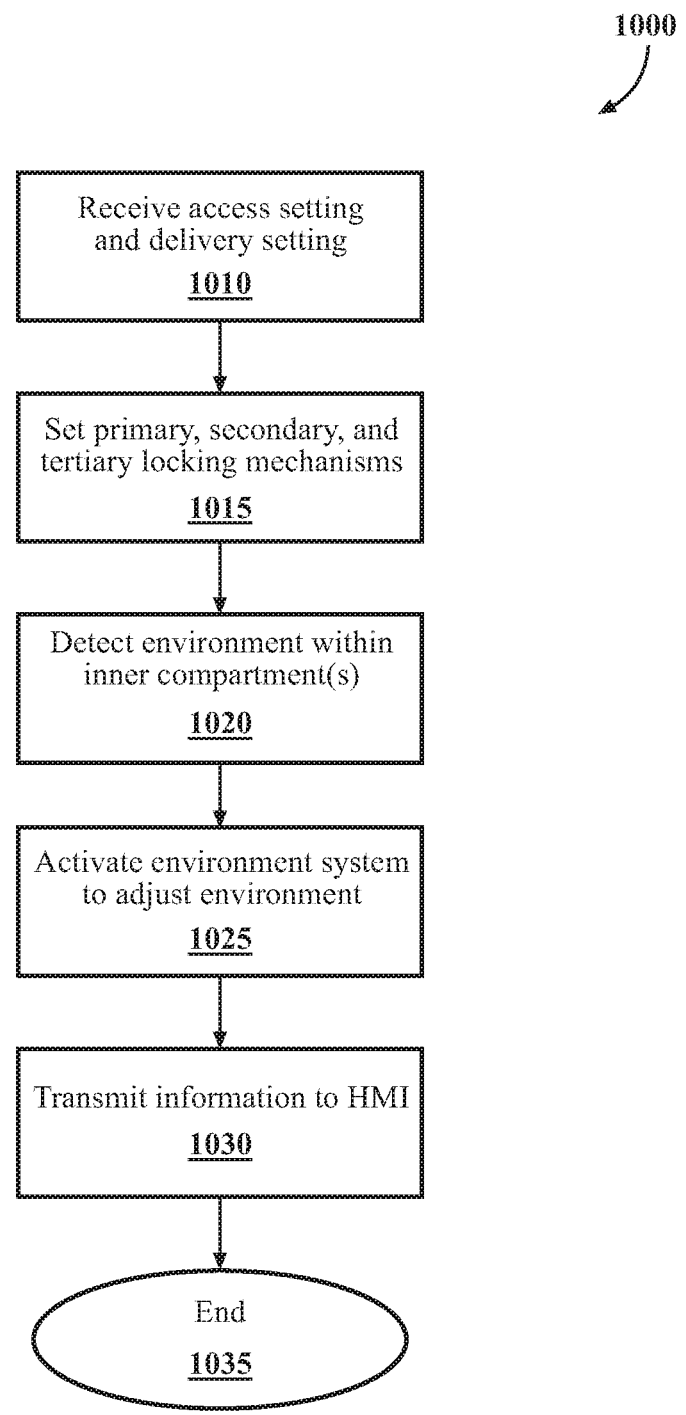
FIG. 11 illustrates a flowchart of a method of implementing and controlling a storage system, according to the disclosed embodiments.

FIG. 11 illustrates a flowchart of a method 1000 of operation a storage system 170 according to the disclosed embodiments. Although the method 1000 will be discussed from the perspective of the storage system 170 of FIG. 2, it should be understood that the method 1000 is not limited to implementation within the storage system 170, which is merely one example of a system that may implement the method 1000. It should further be understood that the order of operations can change in various implementations of the method 1000.

At operation 1010, after a participant of a crowdsourced parcel delivery system 300 accepts a delivery task (e.g., to store and/or deliver a parcel), the storage system 170 receives access settings and delivery settings. The access settings and the delivery settings can be received, for example, directly from the crowdsourced parcel delivery system 300 or inputted into the storage system 170 by the participant. The access settings and the delivery settings can be associated with a given inner compartment 201 of the storage system 170. The storage system 170 can store the delivery settings as delivery criteria data 260 in the database 119 and store the access settings as access data 270 in the database 119.

At operation 1015, the storage system 170 (e.g., locking module 230) sets the primary electronic locking mechanism (e.g., which secures the trunk of the vehicle or the lid of storage unit 290) and at least one secondary electronic locking mechanism (e.g., which secures an inner compartment, e.g., 201) to open in response, respectively, to a primary code and a secondary code based at least in part on information received in the access setting. In one or more embodiments, the parcel is delivered inside a secure container having a tertiary locking mechanism, and the locking module 230 sets the tertiary locking mechanism to unlock in response to a tertiary code determined based at least in part on information received in the access setting. In this manner three layers of security are applied to protect the parcel.

In one or more embodiments, the locking module 230 assigns a validity period to the codes, such that the codes are only valid to unlock the primary locking mechanism, the secondary locking mechanism and the tertiary locking mechanism for a predetermined window of time (e.g., between 1:00 and 1:30). The window of time can be determined based on the access settings, i.e., transmitted from the crowdsourced parcel delivery system 300 or inputted by the participant.

At operation 1020, the storage system 170 (e.g., control module 220) detects an environment inside at least one of the inner compartments based at least in part on data from one or more sensors disposed in the at least one of the inner compartments and activates one or more environment systems to adjust the environment based at least in part on the delivery setting. For example, in one or more embodiments the crowdsourced parcel delivery system 300 can transmit delivery settings that the customer requests be implemented during delivery of the parcel, such as one or more of a desired temperature level, a UV sanitation level, a ventilation level, and a humidity level. For example, for a given order a customer may request that the parcel be transported in a UV sanitated compartment that is maintained at a warm temperature. The crowdsourced parcel delivery system 300 can transmit the request to the storage system 170 in the form of delivery settings that define one or more environment parameters for the inner compartment that will be holding the parcel.

The control module 220 can store the received delivery settings in the database 119 as delivery criteria data 260. Furthermore, the control module 220 can store sensor data obtained from one or more sensors in the inner compartments as environment data 280 in the database 119. In one or more embodiments, the delivery criteria data 260 and the environment data 280 can be stored on a per compartment basis, i.e., the control module 220 can store and update delivery criteria data 260 and environment data 280 associated with each inner compartment 201-207 individually.

At operation 1025, based on the environment data 280 and the delivery criteria data 260 for any given inner compartment 201-207, the control module 220 can adjust associated environment systems (e.g., UV lights, heating/cooling system, HVAC, ventilation system, etc.) to maintain the environment in accordance with the delivery criteria for the duration of the delivery.

At operation 1030, the storage system 170 (e.g., interface module 240) can communicate with a human-machine interface (HMI) of the vehicle 100 and transmit information associated with an environment of at least one of inner compartments to the HMI. For example, the interface module 240 can operate a menu that is displayed on a screen of the vehicle 100 to allow the driver of the vehicle 100 to select an inner compartment and view various information associated with the inner compartment. In one or more embodiments, the information can include current and/or historical environment data 280 or a live feed from a camera sensor installed in the inner compartment. In this manner the driver or owner of the vehicle 100 can remain informed regarding the status of the parcel and the meeting of the delivery requirements and can furthermore take any action necessary in the event that a delivery requirement is not being met due, for example, to a malfunction.

The control module 220, locking module 230 and interface module 240 perform the above-described functions for the duration of the delivery. When the parcel is removed from the storage system 170, the process ends at 1035.

It should be understood that the order of operations in method 1000 may be changed or operated simultaneously.

The embodiments described herein therefore provide a novel storage system which can operate within a crowdsourced parcel delivery system and may be implemented as an aftermarket add-on or incorporated into a vehicle by design, e.g., utilizing the vehicle's existing HVAC, power source, network connection, HMI, remote security, etc. The disclosed storage system can implement a digital key security that requires at least a two-layer security access. In one or more embodiments the storage system can implement a single access code that provides the necessary credentials to access all layers of locking mechanisms or separate access codes may be provided for each locking mechanism. The disclosed storage system can maintain environmental parameters, such as temperature and sanitation, on an individual basis among multiple compartments, thereby facilitating storage and transport of a plurality of parcels that may each have separate and different transport/storage requirements.

FIG. 1 will now be discussed in full detail as an example environment within which the storage system and methods disclosed herein may be installed and operate. In some instances, the vehicle 100 is configured to switch selectively between an autonomous mode, one or more semi-autonomous operational modes, and/or a manual mode. Such switching can be implemented in a suitable manner, now known or later developed. "Manual mode" means that all or a majority of the navigation and/or maneuvering of the vehicle is performed according to inputs received from a user (e.g., human driver). In one or more arrangements, the vehicle 100 can be a conventional vehicle that is configured to operate in only a manual mode.

In one or more embodiments, the vehicle 100 is an autonomous vehicle. As used herein, "autonomous vehicle" refers to a vehicle that operates in an autonomous mode. "Autonomous mode" refers to navigating and/or maneuvering the vehicle 100 along a travel route using one or more computing systems to control the vehicle 100 with minimal or no input from a human driver. In one or more embodiments, the vehicle 100 is highly automated or completely automated. In one embodiment, the vehicle 100 is configured with one or more semi-autonomous operational modes in which one or more computing systems perform a portion of the navigation and/or maneuvering of the vehicle along a travel route, and a vehicle operator (i.e., driver) provides inputs to the vehicle to perform a portion of the navigation and/or maneuvering of the vehicle 100 along a travel route.

The vehicle 100 can include one or more processors 110. In one or more arrangements, the processor(s) 110 can be a main processor of the vehicle 100. For instance, the processor(s) 110 can be an electronic control unit (ECU). The vehicle 100 can include one or more data stores 115 for storing one or more types of data. The data store 115 can include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store 115 can be a component of the processor(s) 110, or the data store 115 can be operatively connected to the processor(s) 110 for use thereby. The term "operatively connected," as used throughout this description, can include direct or indirect connections, including connections without direct physical contact.

In one or more arrangements, the one or more data stores 115 can implement the database 119 (FIG. 2) and can further include map data 116. The map data 116 can include maps of one or more geographic areas. In some instances, the map data 116 can include information or data on roads, traffic control devices, road markings, structures, features, and/or landmarks in the one or more geographic areas. The map data 116 can be in any suitable form. In some instances, the map data 116 can include aerial views of an area. In some instances, the map data 116 can include ground views of an area, including 360-degree ground views. The map data 116 can include measurements, dimensions, distances, and/or information for one or more items included in the map data 116 and/or relative to other items included in the map data 116. The map data 116 can include a digital map with information about road geometry. The map data 116 can be high quality and/or highly detailed.

In one or more arrangements, the map data 116 can include one or more terrain maps 117. The terrain map(s) 117 can include information about the ground, terrain, roads, surfaces, and/or other features of one or more geographic areas. The terrain map(s) 117 can include elevation data in the one or more geographic areas. The map data 116 can be high quality and/or highly detailed. The terrain map(s) 117 can define one or more ground surfaces, which can include paved roads, unpaved roads, land, and other things that define a ground surface.

In one or more arrangements, the map data 116 can include one or more static obstacle maps 118. The static obstacle map(s) 118 can include information about one or more static obstacles located within one or more geographic areas. A "static obstacle" is a physical object whose position does not change or substantially change over a period of time and/or whose size does not change or substantially change over a period of time. Examples of static obstacles include trees, buildings, curbs, fences, railings, medians, utility poles, statues, monuments, signs, benches, furniture, mailboxes, large rocks, hills. The static obstacles can be objects that extend above ground level. The one or more static obstacles included in the static obstacle map(s) 118 can have location data, size data, dimension data, material data, and/or other data associated with it. The static obstacle map(s) 118 can include measurements, dimensions, distances, and/or information for one or more static obstacles. The static obstacle map(s) 118 can be high quality and/or highly detailed. The static obstacle map(s) 118 can be updated to reflect changes within a mapped area.

As noted above, the vehicle 100 can include the sensor system 120. The sensor system 120 can include one or more sensors. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process.

In arrangements in which the sensor system 120 includes a plurality of sensors, the sensors can work independently from each other. Alternatively, two or more of the sensors can work in combination with each other. In such case, the two or more sensors can form a sensor network. The sensor system 120 and/or the one or more sensors can be operatively connected to the processor(s) 110, the data store(s) 115, and/or another element of the vehicle 100 (including any of the elements shown in FIG. 1). The sensor system 120 can acquire data of at least a portion of the external environment of the vehicle 100 (e.g., nearby vehicles).

The sensor system 120 can include any suitable type of sensor. Various examples of different types of sensors will be described herein. However, it will be understood that the embodiments are not limited to the particular sensors described. The sensor system 120 can include one or more vehicle sensors 121. The vehicle sensor(s) 121 can detect, determine, and/or sense information about the vehicle 100 itself. In one or more arrangements, the vehicle sensor(s) 121 can be configured to detect, and/or sense position and orientation changes of the vehicle 100, such as, for example, based on inertial acceleration. In one or more arrangements, the vehicle sensor(s) 121 can include one or more accelerometers, one or more gyroscopes, an inertial measurement unit (IMU), a dead-reckoning system, a global navigation satellite system (GNSS), a global positioning system (GPS), a navigation system 147, and/or other suitable sensors. The vehicle sensor(s) 121 can be configured to detect, and/or sense one or more characteristics of the vehicle 100. In one or more arrangements, the vehicle sensor(s) 121 can include a speedometer to determine a current speed of the vehicle 100.

Alternatively, or in addition, the sensor system 120 can include one or more environment sensors 122 configured to acquire, and/or sense driving environment data. "Driving environment data" includes data or information about the external environment in which an autonomous vehicle is located or one or more portions thereof. For example, the one or more environment sensors 122 can be configured to detect, quantify and/or sense obstacles in at least a portion of the external environment of the vehicle 100 and/or information/data about such obstacles. Such obstacles may be stationary objects and/or dynamic objects. The one or more environment sensors 122 can be configured to detect, measure, quantify and/or sense other things in the external environment of the vehicle 100, such as, for example, lane markers, signs, traffic lights, traffic signs, lane lines, crosswalks, curbs proximate the vehicle 100, off-road objects, etc.

Various examples of sensors of the sensor system 120 will be described herein. The example sensors may be part of the one or more environment sensors 122 and/or the one or more vehicle sensors 121. However, it will be understood that the embodiments are not limited to the particular sensors described.

As an example, in one or more arrangements, the sensor system 120 can include one or more radar sensors 123, one or more LIDAR sensors 124, one or more sonar sensors 125, and/or one or more cameras 126. In one or more arrangements, the one or more cameras 126 can be high dynamic range (HDR) cameras or infrared (IR) cameras.

The vehicle 100 can include an input system 130. An "input system" includes any device, component, system, element or arrangement or groups thereof that enable information/data to be entered into a machine. The input system 130 can receive an input from a vehicle passenger (e.g., a driver or a passenger). The vehicle 100 can include an output system 135. An "output system" includes any device, component, or arrangement or groups thereof that enable information/data to be presented to a vehicle passenger (e.g., a person, a vehicle passenger, etc.). The input system 130 and the output system 135 can be incorporated into the HMI as described above.

The vehicle 100 can include one or more vehicle systems 140. Various examples of the one or more vehicle systems 140 are shown in FIG. 1. However, the vehicle 100 can include more, fewer, or different vehicle systems. It should be appreciated that although particular vehicle systems are separately defined, each or any of the systems or portions thereof may be otherwise combined or segregated via hardware and/or software within the vehicle 100. The vehicle 100 can include a propulsion system 141, a braking system 142, a steering system 143, throttle system 144, a transmission system 145, a signaling system 146, and/or a navigation system 147. Each of these systems can include one or more devices, components, and/or a combination thereof, now known or later developed.

The navigation system 147 can include one or more devices, applications, and/or combinations thereof, now known or later developed, configured to determine the geographic location of the vehicle 100 and/or to determine a travel route for the vehicle 100. The navigation system 147 can include one or more mapping applications to determine a travel route for the vehicle 100. The navigation system 147 can include a global positioning system, a local positioning system or a geolocation system.

The processor(s) 110 and/or the autonomous driving module(s) 160 can be operatively connected to communicate with the various vehicle systems 140 and/or individual components thereof. For example, returning to FIG. 1, the processor(s) 110 and/or the autonomous driving module(s) 160 can be in communication to send and/or receive information from the various vehicle systems 140 to control the movement, speed, maneuvering, heading, direction, etc. of the vehicle 100. The processor(s) 110 and/or the autonomous driving module(s) 160 may control some or all of these vehicle systems 140 and, thus, may be partially or fully autonomous.

The processor(s) 110 and/or the autonomous driving module(s) 160 can be operatively connected to communicate with the various vehicle systems 140 and/or individual components thereof. For example, returning to FIG. 1, the processor(s) 110 and/or the autonomous driving module(s) 160 can be in communication to send and/or receive information from the various vehicle systems 140 to control the movement, speed, maneuvering, heading, direction, etc. of the vehicle 100. The processor(s) 110 and/or the autonomous driving module(s) 160 may control some or all of these vehicle systems 140.

The processor(s) 110 and/or the autonomous driving module(s) 160 may be operable to control the navigation and/or maneuvering of the vehicle 100 by controlling one or more of the vehicle systems 140 and/or components thereof. For instance, when operating in an autonomous mode, the processor(s) 110 and/or the autonomous driving module(s) 160 can control the direction and/or speed of the vehicle 100. The processor(s) 110 and/or the autonomous driving module(s) 160 can cause the vehicle 100 to accelerate (e.g., by increasing the supply of fuel provided to the engine), decelerate (e.g., by decreasing the supply of fuel to the engine and/or by applying brakes) and/or change direction (e.g., by turning the front two wheels). As used herein, "cause" or "causing" means to make, force, compel, direct, command, instruct, and/or enable an event or action to occur or at least be in a state where such event or action may occur, either in a direct or indirect manner.

The vehicle 100 can include one or more actuators 150. The actuators 150 can be any element or combination of elements operable to modify, adjust and/or alter one or more of the vehicle systems 140 or components thereof to responsive to receiving signals or other inputs from the processor(s) 110 and/or the autonomous driving module(s) 160. Any suitable actuator can be used. For instance, the one or more actuators 150 can include motors, pneumatic actuators, hydraulic pistons, relays, solenoids, and/or piezoelectric actuators, just to name a few possibilities.

The vehicle 100 can include one or more modules, at least some of which are described herein. The modules can be implemented as computer-readable program code that, when executed by a processor 110, implement one or more of the various processes described herein. One or more of the modules can be a component of the processor(s) 110, or one or more of the modules can be executed on and/or distributed among other processing systems to which the processor(s) 110 is operatively connected. The modules can include instructions (e.g., program logic) executable by one or more processor(s) 110. Alternatively, or in addition, one or more data store 115 may contain such instructions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

The vehicle 100 can include one or more autonomous driving modules 160. The autonomous driving module(s) 160 can be configured to receive data from the sensor system 120 and/or any other type of system capable of capturing information relating to the vehicle 100 and/or the external environment of the vehicle 100. In one or more arrangements, the autonomous driving module(s) 160 can use such data to generate one or more driving scene models. The autonomous driving module(s) 160 can determine position and velocity of the vehicle 100. The autonomous driving module(s) 160 can determine the location of obstacles, obstacles, or other environmental features including traffic signs, trees, shrubs, neighboring vehicles, pedestrians, etc.

The autonomous driving module(s) 160 can be configured to receive, and/or determine location information for obstacles within the external environment of the vehicle 100 for use by the processor(s) 110, and/or one or more of the modules described herein to estimate position and orientation of the vehicle 100, vehicle position in global coordinates based on signals from a plurality of satellites, or any other data and/or signals that could be used to determine the current state of the vehicle 100 or determine the position of the vehicle 100 with respect to its environment for use in either creating a map or determining the position of the vehicle 100 in respect to map data.

The autonomous driving module(s) 160 can be configured to determine travel path(s) and determine current autonomous driving maneuvers for the vehicle 100, future autonomous driving maneuvers and/or modifications to current autonomous driving maneuvers based on data acquired by the sensor system 120, driving scene models, and/or data from any other suitable source. "Driving maneuver" means one or more actions that affect the movement of a vehicle. Examples of driving maneuvers include: accelerating, decelerating, braking, turning, moving in a lateral direction of the vehicle 100, changing travel lanes, merging into a travel lane, and/or reversing, just to name a few possibilities. The autonomous driving module(s) 160 can be configured can be configured to implement determined driving maneuvers. The autonomous driving module(s) 160 can cause, directly or indirectly, such autonomous driving maneuvers to be implemented. As used herein, "cause" or "causing" means to make, command, instruct, and/or enable an event or action to occur or at least be in a state where such event or action may occur, either in a direct or indirect manner. The autonomous driving module(s) 160 can be configured to execute various vehicle functions and/or to transmit data to, receive data from, interact with, and/or control the vehicle 100 or one or more systems thereof (e.g., one or more of vehicle systems 140).

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-11, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

Generally, modules as used herein include routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™ Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A storage system for implementing crowdsourced delivery of a parcel, comprising:
   a communication system configured to communicate wirelessly with an external server to receive an access setting;
   a storage locker disposed on a vehicle and configured to be secured by a primary electronic locking mechanism, the storage locker including a plurality of inner compartments each configured to be secured by a respective secondary electronic locking mechanism, at least one of the inner compartments including an inner container configured to be secured by a tertiary electronic locking mechanism;
   one or more processors; and
   a memory communicably coupled to the one or more processors and storing a locking module including instructions that when executed by the one or more processors cause the one or more processors to set the primary electronic locking mechanism and at least one secondary electronic locking mechanism to open in response, respectively, to a primary code and a secondary code based at least in part on information received in the access setting,
   wherein the communications system is configured to receive, from the external server, access keys, wherein:
      in response to an operator of the vehicle being responsible for delivering the parcel between handoff locations, the access keys allow the operator to access the storage locker and an inner compartment, but not the inner container, and
      in response to the operator having a need to access the inner container, the access keys allow the operator access to the storage locker, the inner compartment, and the inner container.

2. The storage system of claim 1, further comprising one or more sensors disposed in each of the plurality of inner compartments,
   wherein the communication system is further configured to receive a delivery setting, and the memory further stores:
      a control module including instructions that when executed by the one or more processors cause the one or more processors to detect an aspect of an environment inside the at least one of the plurality of inner compartments based at least in part on data from the one or more sensors and to activate one or more environment systems to adjust the environment based at least in part on the delivery setting.

3. The storage system of claim 2, wherein the one or more environment systems includes an ultra-violet (UV) light system installed in the at least one of the plurality of inner compartments, the UV light system including a plurality of UV lights that direct UV light into the environment within the at least one of the plurality of inner compartments.

4. The storage system of claim 3, wherein the plurality of UV lights are arranged to direct the ultraviolet light toward at least a top, a bottom and a plurality of sides of the parcel when the parcel is placed inside the at least one of the plurality of inner compartments.

5. The storage system of claim 2, wherein the one or more environment systems includes a heating system and/or a cooling system to heat and/or cool the environment inside the at least one of the plurality of inner compartments.

6. The storage system of claim 2, wherein the delivery setting defines one or more environment parameters for at least one of the plurality of inner compartments, the one or more environment parameters being one or more of:
   temperature level,
   UV sanitation level,
   ventilation level, or
   humidity level.

7. The storage system of claim 1, wherein the storage system is integrated in a trunk of the vehicle.

8. The storage system of claim 7, wherein the storage system is connected to and powered by a power system of the vehicle.

9. The storage system of claim 7, wherein the primary electronic locking mechanism is configured to secure the trunk of the vehicle and the locking module further includes instructions to set the trunk to open in response to the primary code based at least in part on information received in the access setting.

10. The storage system of claim 1, wherein the storage system is disposed in a housing mounted on an exterior of the vehicle.

11. The storage system of claim 1, wherein the memory further stores an interface module including instructions that when executed by the one or more processors cause the one or more processors to communicate with a human-machine interface (HMI) of the vehicle and transmit information associated with an environment of at least one of the plurality of inner compartments to the HMI.

12. The storage system of claim 11, further comprising one or more sensors disposed in each of the plurality of inner compartments,
wherein the information further includes one or more of a temperature level, battery power level, or humidity level associated with the at least one of the plurality of inner compartments.

13. The storage system of claim 11, wherein the interface module further includes instructions to control a climate control system to adjust a temperature inside the at least one of the plurality of the inner compartments based on a command received from the HMI.

14. The storage system of claim 1, wherein the plurality of inner compartments includes a first inner compartment having a first set of features, and a second inner compartment having a second set of features different from the first set of features.

15. The storage system of claim 1, wherein the plurality of inner compartments includes a first inner compartment having a first size and/or shape, and a second inner compartment having a second size and/or shape different from the first size and/or shape.

16. The storage system of claim 1, wherein the plurality of inner compartments are formed by partitioning a passenger compartment of the vehicle.

17. A method of controlling a storage system for holding a parcel for delivery, the storage system including a storage locker disposed on a vehicle and configured to be secured by a primary electronic locking mechanism, the storage locker including a plurality of inner compartments each configured to be secured by a respective secondary electronic locking mechanism, at least one of the inner compartments including an inner container configured to be secured by a tertiary electronic locking mechanism, the method comprising:
receiving an access setting;
setting the primary electronic locking mechanism and at least one secondary electronic locking mechanism to open in response, respectively, to a primary code and a secondary code based at least in part on information received in the access setting; and
receiving, from an external server, access keys, wherein:
in response to an operator of the vehicle being responsible for delivering the parcel between handoff locations, the access keys allow the operator to access the storage locker and an inner compartment, but not the inner container, and
in response to the operator having a need to access the inner container, the access keys allow the operator access to the storage locker, the inner compartment, and the inner container.

18. The method of claim 17, further comprising:
receiving a delivery setting;
detecting an aspect of an environment inside the at least one of the plurality of inner compartments based at least in part on data from one or more sensors disposed in the at least one of the plurality of inner compartments; and
activating one or more environment systems to adjust the environment based at least in part on the delivery setting.

19. The method of claim 17, further comprising communicating with a human-machine interface (HMI) of the vehicle to transmit information associated with an environment of at least one of the plurality of inner compartments to the HMI.

20. A system, comprising:
a locker disposed on a vehicle, having an inner compartment, and configured to be secured by a first lock, the inner compartment having an inner container and configured to be secured by a corresponding second lock, the inner container configured to be secured by a third lock;
a processor; and
a communications system configured to receive, from an external server, access keys, wherein:
in response to an operator of the vehicle being responsible for delivering a parcel between handoff locations, the access keys allow the operator to access the locker and the inner compartment, but not the inner container, and
in response to the operator having a need to access the inner container, the access keys allow the operator access to the locker, the inner compartment, and the inner container.

* * * * *